(12) United States Patent
Norfleet

(10) Patent No.: US 6,418,929 B1
(45) Date of Patent: Jul. 16, 2002

(54) INFANT OXYGEN MASK

(76) Inventor: Suzanne H. Norfleet, 14107 Fairhill Ave., Edmond, OK (US) 73103

( * ) Notice: Subject to any disclaimer, the term of this patent is extended or adjusted under 35 U.S.C. 154(b) by 0 days.

(21) Appl. No.: 09/664,150

(22) Filed: Sep. 18, 2000

(51) Int. Cl.$^7$ .............................................. A62B 18/08
(52) U.S. Cl. ............................ 128/207.11; 128/206.27; 128/207.18; 128/207.17; 2/422; 2/206
(58) Field of Search ...................... 128/207.11, 206.27, 128/207.18, 207.17; 2/422, 425, 206, 452, 9

(56) References Cited

U.S. PATENT DOCUMENTS

| | | | | |
|---|---|---|---|---|
| 2,248,477 A | | 7/1941 | Lombard ................... 128/202 |
| 2,383,649 A | * | 8/1945 | Heidbrink .............. 128/206.27 |
| 4,201,205 A | | 5/1980 | Bartholomew ......... 128/205.25 |
| 4,249,529 A | | 2/1981 | Nestor et al. .......... 128/207.17 |
| 4,534,344 A | | 8/1985 | Constance-Hughes . 128/201.15 |
| 4,641,647 A | | 2/1987 | Behan ................... 128/207.18 |
| 5,005,571 A | | 4/1991 | Dietz .................... 128/205.25 |
| D326,540 S | | 5/1992 | Scholey ........................ D29/7 |
| 5,394,568 A | | 3/1995 | Brostrom et al. ............... 2/452 |
| 5,429,683 A | * | 7/1995 | Le Mitouard .......... 128/206.24 |
| 5,464,010 A | * | 11/1995 | Byram .................. 128/207.11 |
| 5,503,147 A | | 4/1996 | Bertheau ............... 128/207.11 |
| 5,570,689 A | | 11/1996 | Starr et al. ............. 128/207.11 |
| 5,617,849 A | | 4/1997 | Springett et al. ...... 128/206.24 |
| 5,770,684 A | | 6/1998 | Stewart et al. .............. 528/392 |
| 5,771,886 A | | 6/1998 | Maire et al. ........... 128/207.11 |
| 5,794,617 A | | 8/1998 | Brunell et al. ......... 128/206.16 |
| 5,921,239 A | | 7/1999 | McCall et al. ......... 128/205.25 |
| 6,112,746 A | * | 9/2000 | Kwok et al. ........... 128/207.13 |

* cited by examiner

*Primary Examiner*—John G. Weiss
*Assistant Examiner*—Michael Mendoza
(74) *Attorney, Agent, or Firm*—Dunlap, Codding & Rogers

(57) ABSTRACT

An oxygen mask for use on an infant is provided. The oxygen mask includes a face mask and a strap assembly connected to the face mask and extendable around the head of the infant for holding the face mask snugly against the infant's face. The strap assembly includes an upper rear strap, a lower rear strap, and a plurality of forward straps. The upper rear strap and the lower rear strap are joined so that the upper and lower rear straps form a loop. A first pair of the forward straps extend from the loop at a first juncture and each strap is adjustably connected to the face mask in a spaced apart relation. Similarly, a second pair of forward straps extend from an opposing side of the loop at a second juncture and are adjustably connected to the face mask in a spaced apart relation. The upper rear strap, the lower rear strap, and the forward straps are sized and oriented relative to one another such that when the face mask and the strap assembly are operably donned on the infant, each of the first and second junctures is positioned substantially above a corresponding ear of the infant, the upper rear strap is positioned across a top side of the infant's head, and the lower rear strap is positioned across a rearward side of the infant's head.

16 Claims, 2 Drawing Sheets

INFANT OXYGEN MASK

CROSS-REFERENCE TO RELATED APPLICATIONS

Not applicable.

BACKGROUND OF THE INVENTION

1. Field of the Invention

The present invention relates generally to devices for securing a mask to the face of an individual, and more particularly, but not by way of limitation, to an oxygen mask for an infant having an improved strap for holding the mask snugly over the infant's nose and mouth.

2. Brief Description of the Related Art

One of the most common problems encountered with new born infants is respiratory distress due to factors including premature birth and poor respiratory effort after birth. Depending on the level of development of the infant's lungs and the degree to which the lungs are distressed, treatment can range from placing the infant on a ventilator to assist the infant's breathing to administering low pressure oxygen so that the infant gets enough oxygen into his bloodstream. With respect to the administering of lower pressure oxygen, this has generally been accomplished with a mask shaped to fit over the nose and mouth of the infant. The mask is held over the nose and mouth of the infant with a single elastic strap which is placed about the infant's head. The mask further includes a flexible tubing to connect the mask to a supply of oxygen.

The posterior side of an infant's head often has an oblong or elongated shape as a result of the child birthing process. Because of this head shape, the single strap used to hold the mask over the infant's nose and mouth tends to slide down the back of the infant's head due to activity by the infant and in turn cause the mask to fall off the infant's face. The rigidity of the oxygen supply tube also has a tendency to cause the mask to be pushed or pulled from the infant's face when the infant is active. It is important, however, that the oxygen mask remain securely in place over on the infant's face at all times to prevent injury to the infant.

To this end, a need has long existed for an oxygen mask for use on an infant that employs a strap which will secure the oxygen mask over the nose and mouth of the infant and which can be donned over the infant's head quickly and easily. It is to such an apparatus that the present invention is directed.

BRIEF SUMMARY OF THE INVENTION

The present invention is directed to an oxygen mask for use on an infant. The oxygen mask includes a face mask and a strap assembly connected to the face mask and extendable around the head of the infant for holding the face mask snugly against the infant's face. The face mask has a rim with an upper portion configured to substantially conform to the contour of the nose bridge of the infant, a first side portion and an opposite second side portion configured to substantially conform to contour of the cheek's of the infant, and a lower portion configured to substantially conform to the contour of the face of the infant below the mouth so as to form a breathing chamber about the mouth and nostrils of the infant when the face mask is positioned on the infant's face.

The strap assembly includes an upper rear strap, a lower rear strap, and a plurality of forward straps. The upper rear strap and the lower rear strap are joined so that the upper and lower rear straps form a loop. A first pair of the forward straps extend from the loop at a first juncture and each strap is adjustably connected to the face mask proximate the first side of the rim in a spaced apart relation. Similarly, a second pair of forward straps extend from an opposing side of the loop at a second juncture and are adjustably connected to the face mask proximate the second side of the rim in a spaced apart relation. The upper rear strap, the lower rear strap, and the forward straps are sized and oriented relative to one another such that when the face mask and the strap assembly are operably donned on the infant, each of the first and second junctures is positioned substantially above a corresponding ear of the infant, the upper rear strap is positioned across a top side of the infant's head, and the lower rear strap is positioned across a rearward side of the infant's head.

In another aspect, the present invention is directed to a method of holding a face mask snugly against an infant's face. The method includes providing a strap assembly having an upper rear strap, a lower rear strap, and a plurality of forward straps. The upper rear strap and the lower rear strap are joined so that the upper and lower rear straps form a loop. A first pair of the forward straps extend from the loop at a first juncture and are adjustably connected to one side of the face mask in a spaced apart relation and a second pair of forward straps extend from an opposing side of the loop at a second juncture and are adjustably connected to the other side of the face mask in a spaced apart relation. The strap assembly is placed about the infant's head such that each of the first and second junctures of the strap assembly is positioned above a corresponding ear of the infant and the upper rear strap portion extends across a top side of the infant's head and the lower rear strap portion extends across a rearward side of the infant's head.

The features and advantages of the present invention will become apparent from the following detailed description when read in conjunction with the accompanying drawings and appended claims.

DETAILED DESCRIPTION OF THE INVENTION

Figure 1:
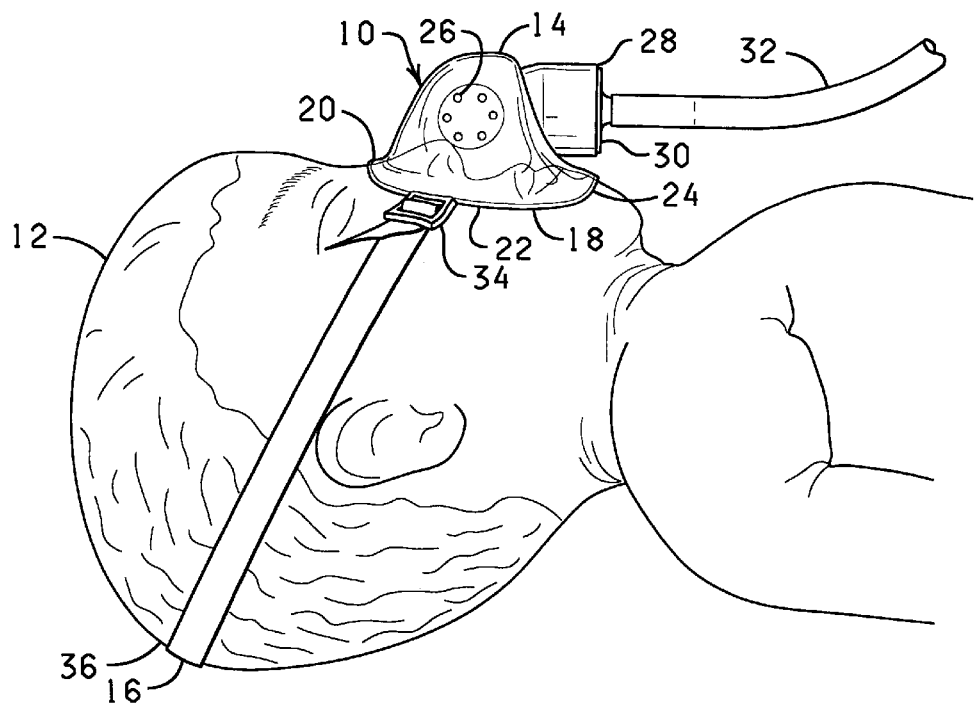
FIG. 1 is a side elevational view of an infant shown with a prior art infant oxygen mask positioned over the infant's nose and mouth.
Figure 2:
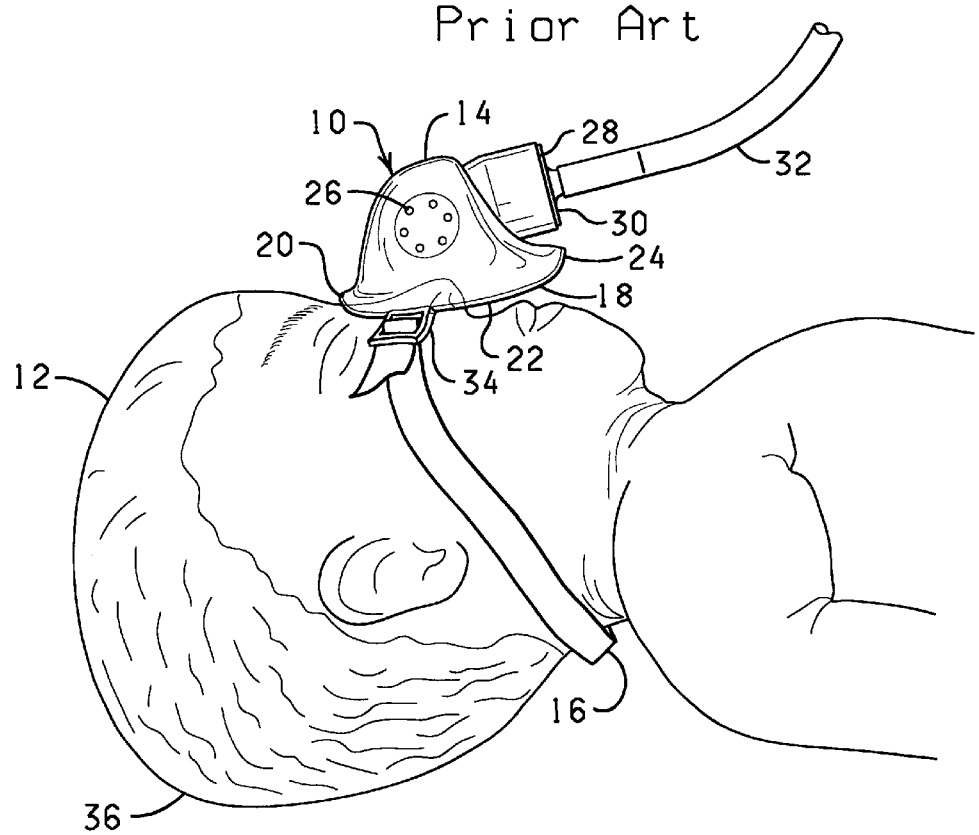
FIG. 2 is a side elevational view of the infant shown in FIG. 1 illustrating the strap of the infant oxygen mask having slid down the back of the infant's head.

Referring now to the drawings and more particularly to FIGS. 1 and 2, a typical prior art oxygen mask 10 of the type adapted to be positioned over the mouth and nose of an infant is shown donned on the face of an infant 12. The oxygen mask 10 includes a face mask 14 and a strap 16 connected to the face mask 14 and extendable around the head of the infant for holding the face mask 14 snugly against the infant's face. The face mask 14 has a rim 18 with an upper portion 20 configured to substantially conform to the contour of the nose bridge of the infant 12, a first side portion 22 and an opposite second side portion (not visible) configured to substantially conform to contour of the cheek's of the infant 12, and a lower portion 24 configured to substantially conform to the contour of the face of the infant 12 below the mouth so as to form a breathing chamber about the mouth and nostrils of the infant 12 when the face mask 14 is positioned on the infant's face. The face mask 14 is normally constructed of a soft, resilient and flexible material, such as PVC (polyvinyl chloride). The face mask 14 is provided with a plurality of vent holes 26 on each side of the face mask 14. The face mask 14 further includes an opening 28 for receiving an adapter plug 30 which has a barbed end (not visible) for receiving one end of an oxygen supply tubing 32. The face mask 14 is further provided with a slotted tab 34 on each side of the face mask 14 for receiving one end of the strap 16. The face mask 14 may be provided with a soft, metal strip (not shown) which is secured to the face mask 14 so as to be positioned across the bridge of the infant's nose when the face mask 14 is in position to assist the face mask 14 in conforming to the general contour of the infant's face.

As mentioned above, an infant's head often has an oblong or elongated shape as a result of the child birthing process. This elongated shape is characterized by a crown 36 generally formed on the posterior side of the infant's head. As such, the portion of the head positioned forward of the crown 36 slopes generally down toward the forehead and the portion of the head positioned rearward of the crown 36 slopes generally down to the neck. As a result, the single strap 16 used to hold the face mask 14 against the infant's face tends to slide over or down the infant's head upon any activity by the infant, as illustrated in FIG. 2. Once the tension of the strap 16 is reduced, the face mask 14 is allowed to fall off the infant's face.

Another problem encountered with the use of the strap 16 to hold the face mask 14 against the face of the infant 12 is that the face mask 14 can be easily pivoted about the axis defined by the two points where the strap 16 is attached to the face mask 14 due to the small size of the face mask 14. This problem is aggravated from the fact that the oxygen supply tubing 32 is relatively rigid along its longitudinal axis. As such, movement by the infant 12 can cause the face mask 14 to be pushed or pulled from the infant's face.

Because of the problems experienced when employing the strap 16 of the prior art to hold the face mask 14 against the face of an infant, a need for an improved strap has long been recognized. However, such improved strap must be capable of holding the face mask snugly against the face of the infant without resulting in injury to the infant. Such improved strap must also be easily positioned about the infant head, quick and easy to adjust, and inexpensive to manufacture.

Figure 3:
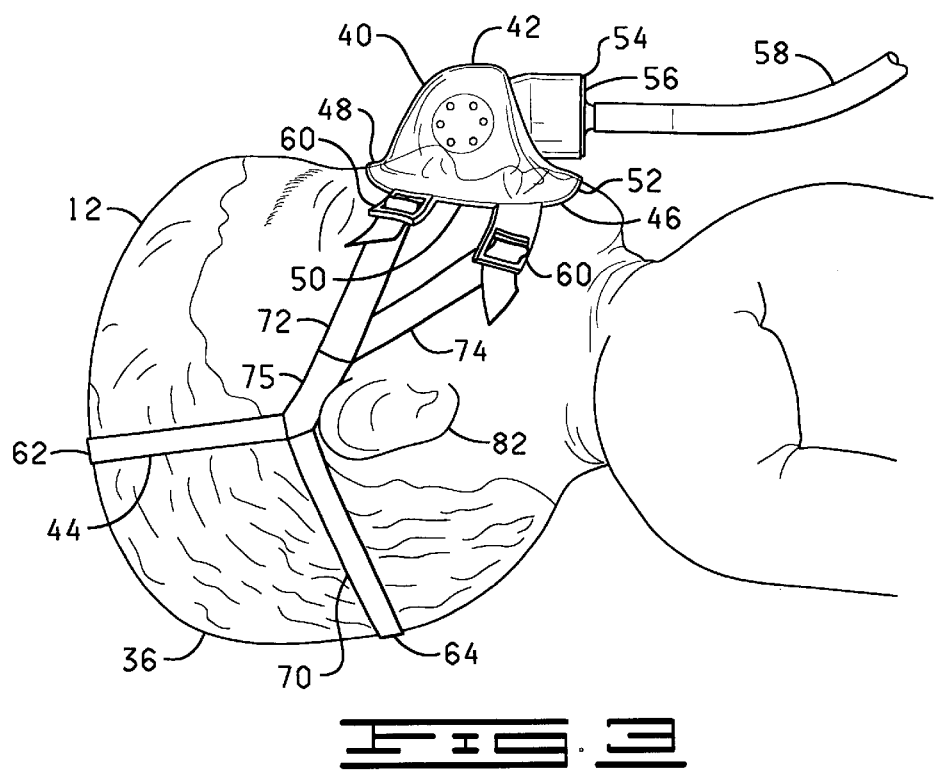
FIG. 3 is a side elevational view of an infant shown with an infant oxygen mask constructed in accordance with the present invention secured over the infant's nose and mouth.

Referring now to FIG. 3, an oxygen mask 40 constructed in accordance with the present invention is illustrated. The oxygen mask 40 overcomes the above mentioned deficiencies of the prior art oxygen mask 10 (FIGS. 1 and 2), and thus the oxygen mask 40 represents an advance in the state of the art relating respiratory devices.

The oxygen mask 40 is illustrated in FIG. 3 donned on the face of the infant 12. The oxygen mask 40 includes a face mask 42 and a strap assembly 44 connected to the face mask 42 and extendable around the head of the infant 12 for holding the face mask 42 snugly against the infant's face. Like the face mask 14 described above, the face mask 42 has a rim 46 with an upper portion 48 configured to substantially conform to the contour of the nose bridge of the infant 12, a first side portion 50 and an opposite second side portion (not visible) configured to substantially conform to contour of the cheek's of the infant 12, and a lower portion 52 configured to substantially conform to the contour of the face of the infant 12 below the mouth so as to form a breathing chamber about the mouth and nostrils of the infant 12 when the face mask 42 is positioned on the infant's face.

The face mask 42 is constructed of a soft, resilient and flexible material, such as PVC (polyvinyl chloride). It is preferable that the face mask 42 be fabricated of a clear material to aid in observing the color of an infant's mucosa and the movement of the infant's nostrils. The face mask 14 further includes an opening 54 for receiving an adapter plug 56 which has a barbed end (not shown) for receiving one end of an oxygen supply tubing 58. The face mask 42 may be provided with a soft, metal strip (not shown) which is secured to the face mask 42 so as to be positioned across the bridge of the infant's nose when the face mask 42 is in position to assist the face mask 42 in conforming to the general contour of the infant's face. Finally, the face mask 42 is provided with a pair of spaced apart, slotted tabs 60 on each side of the face mask 42, or some other suitable structure, for receiving the strap assembly 44.

Figure 4:
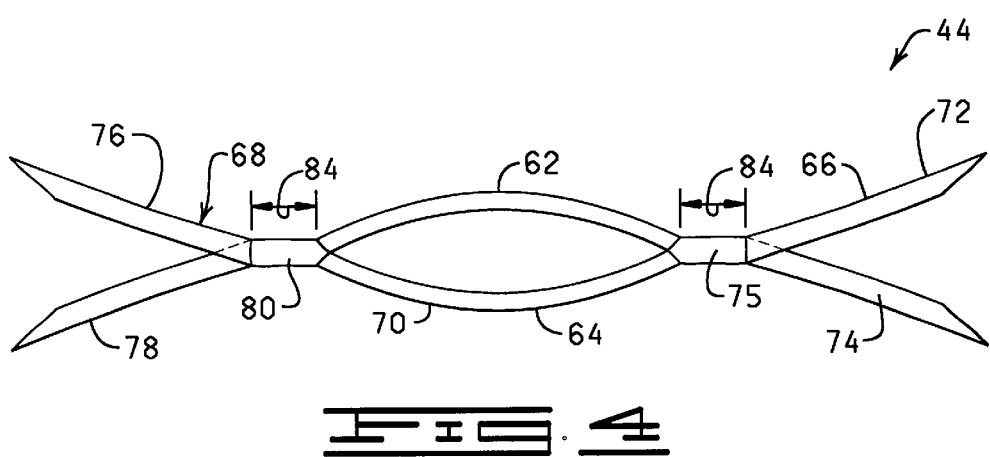
FIG. 4 is a plan view of a strap assembly used with the infant oxygen mask of the present invention shown in a flattened condition.

Referring now to FIG. 4, the strap assembly 44 includes an upper rear strap 62, a lower rear strap 64, a first pair of forward straps 66, and a second pair of forward straps 68. The upper rear strap 62 and the lower rear strap 64 are joined to form a loop 70 which is positionable about the crown 36 of the infant 12. The first pair of the forward straps 66 includes an upper strap 72 and a lower strap 74. Each of the upper strap 72 and the lower strap 74 has an end joined to the loop 70 at a first juncture 75 such that the upper and lower straps 72 and 74 extend from the loop 70 in a diverging relationship whereby the diverged ends of the upper and lower straps 72 and 74 are connectable to the corresponding tab 60 of the face mask 42 by threading the ends of the upper and lower straps 72 and 74 through the slots of the tab 60.

Similarly, the second pair of the forward straps 68 includes an upper strap 76 and a lower strap 78. Each of the upper strap 76 and the lower strap 78 of the second pair of forward straps 68 has an end joined to the loop 70 at a second juncture 80 which is opposite the first juncture 75 such that the upper and lower straps 76 and 78 extend from the loop 70 in a diverging relationship whereby the diverged ends of the upper and lower straps 76 and 78 are connectable to the corresponding tabs 60 of the face mask 42 by threading the ends of the upper and lower straps 76 and 78 through the slots of the tab 60.

The upper rear strap 62, the lower rear strap 64, and the forward straps 72, 74, 76 and 78 are each constructed of an elastic material and sized and oriented relative to one another such that when the face mask 42 and the strap assembly 44 are operably donned on the infant 12, each of the first and second junctures 75 and 80 is positioned substantially above a corresponding ear 82 of the infant 12. To reduce contact with the infant's ears 82, each of the first and second junctures 75 and 80 is formed to have an elongated shape such that the first and second junctures 75 and 80 each have a length 84 which extends approximately from a front side of the infant's ear 82 to a rear side of the infant's ear 82 when the face mask 42 and the strap assembly 44 are operably donned on the infant 12. As such, the upper rear strap 62 is positionable across a top side of the infant's head and the lower rear strap 64 is positioned across a rearward side of the infant's head thereby cooperating with one another to prevent migration of the strap assembly 44 along the infant's head. More specifically, the upper and lower rear straps 62 and 64 are able to be positioned on each side of the crown 36 of the infant's head which is formed on the posterior side of the infant's head as a result of the stress applied to the infant's soft head during the birthing process. In addition, each of the forward straps 72, 74, 76 and 78 is extendible to the face mask 42 such that the forward straps 72, 74, 76 and 78 cooperate with one another to reduce the ability of the face mask 42 to rotate on the infant's face in an upward or downward direction.

It will be appreciated by those of ordinary skill in the art that the strap assembly 44 of the present invention can be constructed in a variety of different ways so long as the strap assembly 44 functions as described herein. For example, the strap assembly 44 can be constructed from six separate straps which are in turn joined to one another, such as by sewing or with a suitably adhesive, to produce the strap assembly 44. Further, the strap assembly 44 can be formed from a pair of straps wherein one of the straps forms the upper forward straps and the lower rear strap and the other strap forms the lower forward straps and the upper rear strap with the two straps being crisscrossed and joined at the first and second junctures 75 and 80. Similarly, the strap assembly 44 can be formed from a pair of straps wherein one of the straps forms the upper forward straps and the upper rear strap and the other strap forms the lower forward straps and the lower rear strap with the two straps being joined at the first and second junctures 75 and 80. Still yet, the strap assembly 44 can be formed single strap which is split to form the forward straps 72, 74, 76 and 78 and the upper and lower rear straps 62 and 64.

In use, the upper and lower forward straps 72, 74, 76 and 78 are threaded through the tabs 60 of the face mask 42. The face mask 42 is then placed over the infant's face and the strap assembly 44 is placed about the infant's head such that the each of first and second junctures 75 and 80 of the strap assembly 44 is positioned above the corresponding ear 82 of the infant 12 and the upper rear strap 62 extends across a top side of the infant's head and the lower rear strap 64 extends across a rearward side of the infant's head. The tension of the forward straps 72, 74, 76 and 78 may be adjusted as necessary to ensure that the rim 46 of the face mask 42 is held snugly against the face of the infant 12.

From the above description it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

What is claimed is:

1. An oxygen mask for use on an infant, comprising:

a face mask having a rim with an upper portion configured to substantially conform to the contour of the nose bridge of the infant, a first side portion and an opposite second side portion configured to substantially conform to contour of the cheek's of the infant, and a lower portion configured to substantially conform to the contour of the face of the infant below the mouth so as to form a breathing chamber about the mouth and nostrils of the infant when the face mask is positioned on the infant's face; and a strap assembly connected to the face mask and extendable around the head of the infant for holding the face mask snugly against the infant's face, the strap assembly comprising an upper rear strap, a lower rear strap, and a plurality of forward straps, the upper rear strap and the lower rear strap being joined so that the upper and lower rear straps form a loop, a first pair of the forward straps extending from the loop at a first juncture and being connected to the face mask proximate the first side of the rim in a spaced apart relation to one another and a second pair of forward straps extending from an opposing side of the loop at a second juncture and being connected to the face mask proximate the second side of the rim in a spaced apart relation to one another, the upper rear strap, the lower rear strap, and the forward straps being sized and oriented relative to one another such that when the face mask and the strap assembly are operably donned on the infant each of the first and second junctures is positioned substantially above a corresponding ear of the infant and has a length which extends approximately from a front side of the infant's ear to a rear side of the infant's ear and the upper rear strap is positioned across a top side of the infant's head and the lower rear strap is positioned across a rearward side of the infant's head.

2. The oxygen mask of claim 1 wherein each of the upper rear strap, the lower rear strap and the forward strap is constructed of an elastic material.

3. The oxygen mask of claim 1 wherein each of the forward straps is adjustably connected to the face mask.

4. An oxygen mask for use on an infant having an elongated head with a crown formed generally on the posterior side of the head, comprising:

a face mask having a rim with an upper portion configured to substantially conform to the contour of the nose bridge of the infant, a first side portion and an opposite second side portion configured to substantially conform to contour of the cheek's of the infant, and a lower portion configured to substantially conform to the contour of the face of the infant below the mouth so as to form a breathing chamber about the mouth and nostrils of the infant when the face mask is positioned on the infant's face; and a strap assembly connected to the face mask and extendable around the head of the infant for holding the face mask snugly against the infant's face, the strap assembly comprising an upper rear strap, a lower rear strap, and a plurality of forward straps, the upper rear strap and the lower rear strap being joined so that the upper and lower rear straps form a loop which is positionable about the crown of the infant's head, a first pair of the forward straps extending from the loop at a first juncture and being connected to the face mask proximate the first side of the rim in a spaced apart relation to one another and a second pair of forward straps extending from an opposing side of the loop at a second juncture and being connected to the face mask proximate the second side of the rim in a spaced apart relation to one another, the upper rear strap, the lower rear strap, and the forward straps being sized and oriented relative to one another such that when the face mask and the strap assembly are operably donned on the infant each of the first and second junctures is positioned substantially above a corresponding ear of the infant and has a length which extends approximately from a front side of the infant's ear to a rear side of the infant's ear and the loop formed by the upper rear strap and the lower rear strap is positioned about the crown of the infant's head.

5. The oxygen mask of claim 4 wherein each of the upper rear strap, the lower rear strap and the forward strap is constructed of an elastic material.

6. The oxygen mask of claim 4 wherein each of the forward straps is adjustably connected to the face mask.

7. In an oxygen mask of the type for use on an infant, the oxygen mask including a face mask with a rim having an upper portion configured to substantially conform to the contour of the nose bridge of the infant, a first side portion and an opposite second side portion configured to substantially conform to contour of the cheek's of the infant, and a lower portion configured to substantially conform to the contour of the face of the infant below the mouth so as to form a breathing chamber about the mouth and nostrils of the infant when the face mask is positioned on the infant's face, the improvement comprising:

a strap assembly connectable to the face mask and extendable around the head of the infant for holding the face mask snugly against the infant's face, the strap assembly comprising an upper rear strap, a lower rear strap, and a plurality of forward straps, the upper rear strap and the lower rear strap being joined so that the upper and lower rear straps form a loop, a first pair of the forward straps extending from the loop at a first juncture and being connected to the face mask proximate the first side of the rim in a spaced apart relation to one another and a second pair of forward straps extending from an opposing side of the loop at a second juncture and being connected to the face mask proximate the second side of the rim in a spaced apart relation to one another, the upper rear strap, the lower rear strap, and the forward straps being sized and oriented relative to one another such that when the face mask and the strap assembly are operably donned on the infant each of the first and second junctures is positioned substantially above a corresponding ear of the infant and has a length which extends approximately from a front side of the infant's ear to a rear side of the infant's ear and the upper rear strap is positioned across a top side of the infant's head and the lower rear strap is positioned across a rearward side of the infant's head.

8. The improvement of claim 7 wherein each of the upper rear strap, the lower rear strap and the forward strap is constructed of an elastic material.

9. The oxygen mask of claim 7 wherein each of the forward straps is adjustably connectable to the face mask.

10. In an oxygen mask of the type for use on an infant having an elongated head with a crown formed generally on the posterior side of the head, the oxygen mask including a face mask with a rim having an upper portion configured to substantially conform to the contour of the nose bridge of the infant, a first side portion and an opposite second side portion configured to substantially conform to contour of the cheek's of the infant, and a lower portion configured to substantially conform to the contour of the face of the infant below the mouth so as to form a breathing chamber about the mouth and nostrils of the infant when the face mask is positioned on the infant's face, the improvement comprising:

a strap assembly connectable to the face mask and extendable around the head of the infant for holding the face mask snugly against the infant's face, the strap assembly comprising an upper rear strap, a lower rear strap, and a plurality of forward straps, the upper rear strap and the lower rear strap being joined so that the upper and lower rear straps form a loop which is positionable about the crown of the infant's head, a first pair of the forward straps extending from the loop at a first juncture and being connected to the face mask proximate the first side of the rim in a spaced apart relation to one another and a second pair of forward straps extending from an opposing side of the loop at a second juncture and being connected to the face mask proximate the second side of the rim in a spaced apart relation to one another, the upper rear strap, the lower rear strap, and the forward straps being sized and oriented relative to one another such that when the face mask and the strap assembly are operably donned on the infant each of the first and second junctures is positioned substantially above a corresponding ear of the infant and has a length which extends approximately from a front side of the infant's ear to a rear side of the infant's ear and the loop formed by the upper rear strap and the lower rear strap is positioned about the crown of the infant's head.

11. The improvement of claim 10 wherein each of the upper rear strap, the lower rear strap and the forward strap is constructed of an elastic material.

12. The oxygen mask of claim 10 wherein each of the forward straps is adjustably connectable to the face mask.

13. A method of holding a face mask snugly against an infant's face, the face mask having a rim with an upper portion configured to substantially conform to the contour of the nose bridge of an infant, a first side portion and an opposite second side portion configured to substantially conform to contour of the cheek's of the infant, and a lower portion configured to substantially conform to the contour of the face of the infant below the mouth so as to form a breathing chamber about the mouth and nostrils of the infant to the face of the infant when the face mask is held against the infant's face, the method comprising:

providing a strap assembly having an upper rear strap, a lower rear strap, and a plurality of forward straps, the upper rear strap and the lower rear strap being joined so that the upper and lower rear straps form a loop, a first pair of the forward straps extending from the loop at a first juncture and connected to one side of the face mask in a spaced apart relation and a second pair of forward straps extending from an opposing side of the loop at a second juncture and connected to the other side of the face mask in a spaced apart relation, each of the first and second junctures of the strap assembly having a length which extends approximately from a front side of an infant's ear to a rear side of the infant's ear;

placing the strap assembly about the infant's head such that each of the first and second junctures of the strap assembly is positioned above a corresponding ear of the infant and extends approximately from the front side of the infant's ear to the rear side of the infant's and the upper rear strap extends across a top side of the infant's head and the lower rear strap extends across a rearward side of the infant's head.

14. The method of claim 13 further comprising adjusting tension of the forward straps.

15. A method of holding a face mask snugly against an infant's face wherein the infant has an elongated head with a crown formed generally on the posterior side of the head, the face mask having a rim with an upper portion configured to substantially conform to the contour of the nose bridge of an infant, a first side portion and an opposite second side portion configured to substantially conform to contour of the cheek's of the infant, and a lower portion configured to substantially conform to the contour of the face of the infant below the mouth so as to form a breathing chamber about the mouth and nostrils of the infant to the face of the infant when the face mask is held against the infant's face, the method comprising:

provided a strap assembly having an upper rear strap, a lower rear strap, and a plurality of forward straps, the upper rear strap and the lower rear strap being joined so that the upper and lower rear straps form a loop which is positionable about the crown of the infant's head, a first pair of the forward straps extending from the loop at a first juncture and connected to one side of the face mask in a spaced apart relation and a second pair of forward straps extending from an opposing side of the loop at a second juncture and connected to the other side of the face mask in a spaced apart relation, each of the first juncture and the second juncture of the strap assembly having a length which extends approximately from a front side of an infant's ear to a rear side of the infant's ear; and placing the strap assembly about the infant's head such that each of the first and second junctures of the strap assembly is positioned above a corresponding ear of the infant and extends approximately from the front side of the infant's ear to the rear side of the infant's and the loop formed by the upper rear strap and the lower rear strap extends about the crown of the infant's head.

16. The method of claim 15 further comprising adjusting tension of the forward straps.

\* \* \* \* \*